United States Patent
Wikström et al.

(10) Patent No.: US 7,745,441 B1
(45) Date of Patent: *Jun. 29, 2010

(54) UROKINASE INHIBITORS

(75) Inventors: Peter Wikström, Gipf-Oberfrick (CH); Helmut Vieweg, Rheinfelden (DE); Jörg Stürzebecher, Erfurt-Rhoda (DE)

(73) Assignee: Wilex AG, Munich (DE)

( * ) Notice: Subject to any disclaimer, the term of this patent is extended or adjusted under 35 U.S.C. 154(b) by 254 days.

This patent is subject to a terminal disclaimer.

(21) Appl. No.: 09/787,647

(22) PCT Filed: Sep. 18, 1998

(86) PCT No.: PCT/CH98/00402

§ 371 (c)(1), (2), (4) Date: Aug. 9, 2001

(87) PCT Pub. No.: WO00/17158

PCT Pub. Date: Mar. 30, 2000

(51) Int. Cl.
A61K 31/495 (2006.01)
A61K 31/445 (2006.01)
C07D 295/185 (2006.01)
C07D 295/192 (2006.01)
C07D 295/20 (2006.01)
C07D 409/12 (2006.01)

(52) U.S. Cl. .................. 514/255.01; 514/330; 544/388; 546/213; 546/226

(58) Field of Classification Search .................. 544/387, 544/388; 546/226; 514/330, 255.01
See application file for complete search history.

(56) References Cited

U.S. PATENT DOCUMENTS

| 5,607,937 | A  | * | 3/1997 | Stuerzebecher et al. | |
| 6,624,169 | B1 | * | 9/2003 | Wilhelm et al. | 514/255.01 |
| 6,680,320 | B2 | * | 1/2004 | Wilhelm et al. | 514/255.01 |
| 7,342,018 | B2 | * | 3/2008 | Wilhelm et al. | 514/255.01 |
| 2003/0013723 | A1 | * | 1/2003 | Wilhelm et al. | |

FOREIGN PATENT DOCUMENTS

| CH | 689611 | * | 7/1999 |
| WO | 00/04954 | * | 2/2000 |

OTHER PUBLICATIONS

Plattner, Annual Reports in Medicinal Chemistry, vol. 34, pp. 121-128 (1999).*
Andreasen et al. Int. J.Cancer vol. 72, pp. 1-22 (1997).*
Renatus et al. J.Med. Chem. vol. 41, pp. 5445-5456 (Dec. 1998).*
Sturzebecher et al. Bioorganic & Medicinal Chemistry Letters vol. 9, pp. 3147-3152 (1999).*
Bernd Muehlenweg, Stefan Sperl, Viktor Magdolen, Manfred Schmitt & Nadia Harbeck, Interference with the urokinase plasminogen activator system: a promising therapy concept for solid tumours, *Expert Opin. Biol. Ther.* (2001) 1(4), 2001 © Ashley Publications Ltd. ISSN 1471-2598, pp. 683-691.
Fritz Jänicke, Anita Prechtl, Christoph Thomssen, Nadia Harbeck, Christoph Meisner, Michael Untch, C. G. J. Fred Sweep, Hans-Konrad Selbmann, Henner Graeff, Manfred Schmitt, Randomized Adjuvant Chemotherapy Trial in High-Risk, Lymph Node-Negative Breast Cancer Patients Identified by Urokinase-Type Plasminogen Activator and Plasminogen Activator Inhibitor Type 1, *Journal of the National Cancer Institute*, vol. 93, No. 12, Jun. 20, 2001, pp. 913-920.
Viktor Magdolen, Nuria Arroyo de Prada, Stefan Sperl, Bernd Muehlenweg, Thomas Luther, Olaf G. Wilhelm, Ulla Magdolen, Henner Graeff, Ute Reuning, and Manfred Schmitt, Natural and Synthetic Inhibitors of the Tumor-Associated Serine Protease Urokinase-Type Plasminogen Activator, *Cellular Peptidases in Immune Functions and Diseases 2*, 2000, Plenum Publishers, pp. 331-341.
M. Schmitt, O. G. Wilhelm, U. Reuning, A. Krüger, N. Harbeck, E. Lengyel, H. Graeff, B. Gänsbacher, H. Kessler, M. Bürgle, J. Stürzebecher, S. Sperl, V. Magdolen, The urokinase plasminogen activator system as a novel target for tumour therapy, *Fibrinolysis & Proteolysis* (2000) 14(2/3), pp. 114-132.
Prefabloc—Series Synthetic Serine Proteinase Inhibitors [4904] (1997).
Pentapharm Product Catalog 1998.
Sturzebecher et al., 1997 Journal of Medical Chemistry 19(40): 3091-3099.
Markwardt et al., 1980 Thrombosis Research 17(3-4) 425-431.
Sturzebecher et al., 1997, Biological Chemistry Hoppe-Seyler 373(10): 1025-1030.
Wagner et al., 1981, Die Pharmazie 36(7): 467-470.
Sturzebecher et al., Die Pharmazie 36(7): 501-502, (1981).

* cited by examiner

*Primary Examiner*—Emily Bernhardt
(74) *Attorney, Agent, or Firm*—Rothwell, Figg, Ernst & Manbeck, P.C.

(57) ABSTRACT

New urokinase inhibitors having a triisopropylphenylsulfonyl residue as an Nα-substituent for 3-amidinophenylalanine are provided. The introduction of the triisopropylphenylsulfonyl residue greatly increases the affinity of the compounds to urokinase and, thereby, increases their inhibitory activity against urokinase. These urokinase inhibitors are useful in determining the role of urokinase and urokinase receptor in various diseases, particularly in tumor propagation and metastasis. Methods of treating tumors and a pharmaceutical composition are also provided.

6 Claims, No Drawings

UROKINASE INHIBITORS

Proteolytic processes play an important part in the propagation and metastasizing of solid tumors. For assembling and disassembling the structures in their immediate environment, they have not only procoagulant substances at their disposal, but also enzymes of the fibrinolytic system. Although the (patho)biochemical connections are not yet definitely elucidated, a central significance is obviously to be attributed to the plasminogen activator urokinase and to the urokinase receptor. Therefore, the development of urokinase inhibitors can be highly useful first of all to further elucidate the role of urokinase and urokinase receptor in different diseases, particularly in tumor propagation and metastasizing. Moreover, urokinase inhibitors represent potential drugs for influencing tumor invasion.

Urokinase is a proteolytic enzyme and belongs to the group of trypsin-like enzymes which, in proteins and peptides, cleave the bonds of the basic amino acids arginine and lysine. Therefore, most inhibitors known until now have a strongly basic group, e.g., an amidino function. The first urokinase inhibitors efficient in the micromolar region were found among bis-benzamidines and naphthamidine-derived compounds (J. Stürzebecher and F. Markwardt, Pharmazie 33, 599-602, 1978). Compounds which also inhibit urokinase with micromolar $K_i$ values and have a guanidino function such as amilorides (J.-D. Vassalli and D. Belin, FEBS Lett. 214, 187-191, 1987) and phenylguanidines (H. Yang et al., J. Med. Chem. 33, 2956-2961, 1990) were described later. Benzothiophene-2-carboxamidines were described as highly effective inhibitors ($K_i$ at 0.2 µmol/l) (M. J. Towle et al., Cancer Res. 53, 2553-2559, 1993).

Nα-arylsulfonylated and Nα-arylsulfonyl-aminoacylated derivatives of 3-amidinophenylalanine are known to be selective inhibitors of thrombin (F. Markwardt et al., Thromb. Res. 17, 425-431, 1980) and of the clotting factor Xa (J. Stürzebecher et al., Thromb. Res. 54, 245-252, 1989), respectively. We have surprisingly found in the variation of the Nα-substituent that the introduction of a triisopropylphenylsulfonyl residue increases the affinity towards urokinase very decisively. Thus, Nα-triisopropylphenylsulfonyl-protected 3-amidinophenylalanine derivatives represent a new group of urokinase inhibitors.

The present invention relates to new urokinase inhibitors of general formula I,

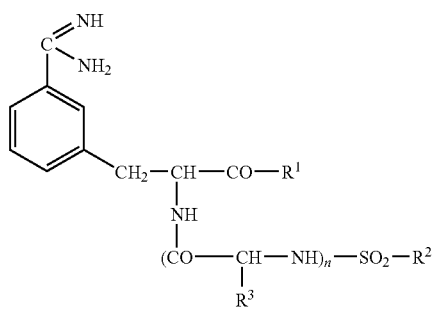

I which are present as racemates as well as compounds in L- or D-form, respectively, and wherein
$R^1$ represents
(a) OH, O-alkyl, branched or unbranched, $C_1$-$C_8$, O-cycloalkyl, $C_5$-$C_8$, O-aralkyl, benzyl or phenylethyl,
(b) a group of formula

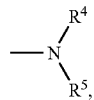

wherein
$R^4$=$R^5$=H, $R^4$=H and $R^5$=branched or unbranched alkyl $C_1$-$C_8$, (un)substituted aralkyl, benzyl or phenylethyl, as well as cycloalkylalkyl $C_5$-$C_8$, $R^4$=$R^5$ equal or unequal and unbranched or branched alkyl $C_1$-$C_4$ as well as $R^4$=H and $R^5$=—NH$_2$ or substituted —NH$_2$, in particular aryl or heteroaryl,
(c) a group of formula

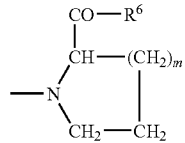

wherein m represents the integer 1 or 2, and wherein one of the methylene groups is possibly substituted with a hydroxyl, carboxyl, low alkyl, $C_1$-$C_4$, or aralkyl residue, benzyl or phenylethyl, the group (c) being a racemate, D- or L-form, respectively, and
$R^6$ has the denotation of $R^1$ in (a), (b) and (f),
(d) a group of formula

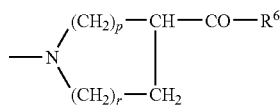

wherein either p=r=1, p=1 and r=2 or p=2 and r=1 and wherein one of the methylene groups is possibly substituted with a hydroxyl, carboxyl, low alkyl, $C_1$-$C_4$ or aralkyl residue, benzyl or phenylethyl, and
$R^6$ has the denotation of $R^1$ in (a), (b) and (f),
(e) a piperidyl group which is possibly substituted with a low alkyl, $C_1$-$C_4$ or hydroxyl residue in one of the positions 2, 3 and 4, wherein a further aromatic or cycloaliphatic ring, preferably phenyl or cyclohexyl, in position 2, 3 or 3,4, related to the heteroatom, is possibly condensed to the heterocycloaliphatic rings of formulas (c), (d) and (e),
(f) a group of formula

wherein $R^7$ represents an alkyl, $C_1$-$C_6$, or (un)substituted aryl residue, e.g. phenyl, p-halogenphenyl or naphthyl, an alkoxy, saturated or unsaturated, branched or unbranched $C_1$-$C_6$, (un)substituted phenoxy or benzyloxycarbonyl residue, respectively,
(g) an acyl residue of formula —COX, wherein X=H or means unbranched or branched, possibly substituted alkyl, preferably low alkyl, $C_1$-$C_6$, in particular methyl, (un)substituted aryl or heteroaryl, e.g. phenyl, p-halogenphenyl, thienyl or (un)substituted cycloalkyl, preferably $C_3$-$C_{10}$, (h) an aralkyl residue, benzyl or phenylethyl, wherein the aromatic residue is substituted with e.g. a halogen atom, an alkyl, $C_1$-$C_6$, alkoxy, $C_1$-$C_3$, hydroxy or nitro group, (i) a carboxamide residue of formula —CONR'R", a thiocarboxamide residue —CSNR'R" or an acetamide residue —$CH_2$—CONR'R", wherein R'=R"=H; R'=R" is equal or unequal alkyl, $C_1$-$C_4$; R'=H, R"=alkyl, $C_1$-$C_4$; R'=H, R"=aryl, phenyl, or R' and R" form with the nitrogen atom a heterocycloaliphatic ring with 5-7 ring members that may carry a further heteroatom N, O, S, (j) an $SO_2$—Y residue, in which Y means (un)substituted alkyl, preferably methyl, trifluoromethyl, trichloromethyl, (un)substituted aryl or heteroaryl, e.g. phenyl, 4-methylphenyl, 2,4,6-trimethyl or triisopropylphenyl, 4-methoxy-2,3,6-trimethylphenyl, 2,2-dimethyl-6-methoxy or 2,2,5,7,8-pentamethylchromanyl, anthrachinonyl, naphthyl or chinolyl respectively O-aryl, preferably phenyl, or —NR'R", wherein R' and R"=H is equal or unequal low alkyl $C_1$-$C_3$, (k) a cycloaliphatic ring with 5 to 8 C atoms which is possibly substituted with a hydroxyl or oxo group, (l) an (un)substituted heteroaryl residue, e.g. pyridyl or pyrimidyl, or a heterocycloaliphatic residue, e.g. N-methylpiperidyl, respectively, (m) a functionalized alkyl residue of formula —$(CH_2)_n$—X, wherein the alkyl chain is unbranched or branched, n=1 to 8 and the functional residue X represents a hydroxyl group, the H atom of which is possibly substituted by an alkyl, $C_1$-$C_4$, aralkyl, benzyl or phenylethyl, aryl, phenyl, hydroxyalkyl, $C_1$-$C_4$, or acyl group, CO-Alk, $C_1$-$C_6$, and means a halogen atom, a tertiary amino group of formula —$N(Alk)_2$, wherein the alkyl groups have 1 to 3 C atoms and the same denotation and the nitrogen atom possibly also has a heterocycloaliphatic ring with 5-7 ring members that may carry a further heteroatom N, O, S, $R^2$ represents branched or unbranched alkyl ($C_1$-$C_{16}$) or an (un)substituted aryl or heteroaryl residue, e.g. phenyl, 4-methylphenyl, 2,4,6-trimethyl or 2,4,6-triisopropylphenyl, 4-methoxy-2,3,6-trimethylphenyl, 2,2-dimethyl-6-methoxy or 2,2,5,7,8-pentamethylchromanyl, anthrachinonyl, 1- or 2-naphthyl, 5-(dimethylamino)-naphthyl, chinolyl or isochinolyl, or a camphor residue, $R^3$=H or represents branched or unbranched alkyl ($C_1$-$C_4$), and n=0 or 1.

The compounds are generally present as salts with inorganic acids, preferably as hydrochlorides, or as salts with appropriate organic acids.

Among the compounds defined in the general claims, those wherein $R^1$ corresponds to a group of formulas (b), (d) and (f), $R^2$ represents a 2,4,6-triisopropylphenyl residue and n=0, are of particular significance.

The compounds of general formula I can be manufactured according to a principally known method, as described hereinafter.

(L)-, (D)- or (D,L)-3-cyanophenylalanine methylester hydrochloride is converted with the corresponding sulfonyl chloride or a sulfonylated amino acid or its halide, respectively, in the presence of a base into a compound corresponding to general formula I, but having a cyano function and wherein $R^1$=—$OCH_3$, and $R^2$ as well as $R^3$ have the denotations defined in the general claims. Compounds of general formula I with a carboxylic acid structure ($R^1$=—OH) are obtained by gentle acidic or alkaline hydrolysis; their esterification with a corresponding alcohol under acid-catalytic conditions leads to the compounds of general formula I wherein $R^1$=(a). According to a method currently applied in peptide chemistry, e.g., DCC in the presence of HOBt, the compounds with a corresponding $R^1$ of general formula I can be represented by conversion of the carboxylic acids corresponding to general formula I ($R^1$=—OH) with a nucleophile of structures (b), (e) and (f). The synthesis of compounds with $R^1$=(c) and (d) requires first the conversion of carboxylic acids corresponding to general formula I, with $R^1$=OH with cycloaliphatic amino acid esters corresponding to structures (c) and (d), wherein $R^6$ preferably means —$OCH_3$ or —$OC_2H_5$, respectively, and then hydrolysis of the obtained carboxylates under gentle acidic or alkaline conditions into the corresponding carboxylic acids which can be subsequently esterified or converted in an already described way with the nucleophiles of structure (b), (e) and (f), whereby compounds corresponding to general formula I with $R^1$=(c) and (d) and $R^6$=(a), (b), (e) and (f) are obtained.

The target compounds of general formula I with an amidine structure can be obtained from cyano compounds in a known way. In general, addition of $H_2S$ to the cyano group first gives thioamides which are converted into thioimidoesters by S-methylation with methyl iodide and finally into amidino compounds by treatment with ammonium acetate in alcoholic solution. Moreover, the corresponding imidoester hydrochlorides can be sometimes represented from the cyano compounds with methanol or ethanol in the presence of HCl gas and in certain cases of an inert solvent; conversion of these hydrochlorides in alcoholic ammonia solution leads to the amidino compounds.

The urokinase inhibitors of the present invention can be used together with at least one appropriate pharmaceutical additive for the preparation of orally, subcutaneously or intravenously administrable drugs for combating tumors or in diagnosis.

Drugs for combating tumors in humans and animals can be administered orally, subcutaneously or intravenously, e.g., in the form of tablets, dragées, capsules, pellets, suppositories, solutions or transdermal systems, such as plasters.

The invention is further explained in the two following examples.

EXAMPLE I

N-α-2,4,6-Triisopropylphenylsulfonyl-(L)-3-amidinophenylalanine-4-ethoxycarbonyl-piperazide hydrochloride

1.1. N-α-2,4,6-Triisopropylphenylsulfonyl-(L)-3-cyanophenylalanine methyl ester 5 g of (L)-3-cyanophenylalanine methyl ester hydrochloride was suspended in 100 ml of dioxane, 4.45 ml of NMM was added and the mixture was stirred for 30 min. After addition of 5.97 g of 2,4,6-triisopropylbenzenesulfonylchloride in a solid form, the mixture was stirred for 3 days, whereupon precipitated NMM.HCl was filtered off, the solvent was evaporated and the obtained crude product was purified over SG 60 (chloroform). Yield: 8.34 g of a syrup (90%).

1.2. N-α-2,4,6-Triisopropylphenylsulfonyl-(L)-3-cyanophenylalanine 8.34 g of compound 1.1 was dissolved in a mixture of 50 ml each of acetic acid and 1 N hydrochloric acid, refluxed for 8 hours, extracted twice with ethyl acetate after cooling, the pooled ethyl acetate solutions were dried over MgSO₄ and the solvent was evaporated. After purification over SG 60 (chloroform) 5.8 g of a solid product was obtained (72%).

1.3. N-α-2,4,6-Triisopropylphenylsulfonyl-(L)-3-cyanophenylalanine-4-ethoxycarbonyl piperazide 5.7 g of compound 1.2 was dissolved in 100 ml of THF, cooled to 0° C., 2.22 g of HOBt and 2.82 g of DCC was added and the mixture was stirred for 30 min. After addition of 3.94 g of 1-ethoxycarbonyl piperazine in 30 ml of THF, the mixture was stirred overnight, whereupon precipitated DCU was filtered off, the solvent was evaporated and the obtained crude product was purified over SG 60 (chloroform). Yield: 7.1 g of an amorphous powder (96%).

1.4. N-α-2,4,6-Triisopropylphenylsulfonyl-(L)-3-amidinophenylalanine-4-ethoxycarbonyl-piperazide hydrochloride 7.1 g of compound 1.3 was dissolved in 30 ml of pyridine, 30 drops of TEA were added, a strong stream of hydrogen sulfide was applied for 10 min and the reaction mixture was let stand for 2 days at room temperature. After evaporation of the solvent, the residue was dissolved in ethyl acetate, the organic phase was washed with 1 N acetic acid and saturated saline, dried over MgSO₄ and the solvent was evaporated. 7.2 g of the thioamide obtained in this way was dissolved in 250 ml of acetone, 17 g of methyl iodide was added to the solution and let stand for 2 days in the dark at room temperature. Afterwards, the solvent was evaporated, the thioimide ester hydroiodide (8.5 g) was dissolved in 50 ml of methanol, 1.9 g of ammonium acetate was added and the mixture was heated for 4 hours at 60° C. The crude product obtained after evaporation of the solvent was purified over LH 20 (methanol). The amidine hydroiodide obtained in this way was converted into hydrochloride over an ion exchanger (Amberlite IRA-420). Yield: 5.3 g of an amorphous powder (69%).

EXAMPLE 2

Nα-2,4,6-Triisopropylphenylsulfonyl-(D,L)-3-amidinophenylalanyl-nipecotic acid-benzylamide hydrochloride

2.1. Nα-2,4,6-Triisopropylphenylsulfonyl-(D,L)-3-cyanophenylalanyl-nipecotic acid ethyl ester 4.57 g of Nα-2,4,6-triisopropylphenylsulfonyl-(D,L)-3-cyanophenylalanine (from (D,L)-3-cyanophenylalanine methyl ester hydrochloride and the corresponding sulfonyl chloride as represented in 1.1 and 1.2), 1.5 g of HOBt and 2.42 g of DCC were dissolved in 50 ml of DMF and stirred for 1 hour, whereupon 2.36 g of nipecotic acid ethyl ester was added. After stirring overnight, precipitated DCU was filtered off, the solvent was evaporated, the residue was dissolved in few methanol and the product allowed to crystallize. The formed precipitate was filtered off, washed with methanol and dried. Yield: 4.46 g (75%).

2.2. Nα-2,4,6-Triisopropylphenylsulfonyl-(D,L)-3-cyanophenylalanyl-nipecotic acid 4.4 g of the previously described ethyl ester was dissolved in a mixture composed of 35 ml of acetic acid and 25 ml of 1 N HCl and refluxed for 2 hours. After addition of 10 ml of water, the reaction mixture was cooled down, whereby a wax-like product precipitated. After discarding the solvent, 200 ml of water was added, the mixture was vigorously stirred for a prolonged period of time and the solid substance obtained was filtered off, washed with water and dried. Yield: 3.84 g (92%).

2.3. Nα-2,4,6-Triisopropylphenylsulfonyl-(D,L)-3-cyanophenylalanyl-nipecotic acid benzylamide 2.28 g of the previously described compound, 0.6 g of HOBt and 0.97 g of DCC was dissolved in 20 ml of DMF, stirred for 1 hour, 0.6 g of benzylamine was added and the mixture was further stirred overnight. After filtration of the precipitated DCU, the solvent was evaporated, the residue was dissolved in methanol and the solution was poured into 5% sodium hydrogen carbonate solution/ice. After 1 hour the formed precipitate was filtered off, washed with water and dried under high vacuum. Yield: 2.48 g (94%).

2.4. Nα-2,4,6-Triisopropylphenylsulfonyl-(D,L)-3-amidinophenylalanyl-nipecotic acid-benzylamide hydrochloride 2.4 g of compound 2.3 was dissolved in 30 ml of pyridine, 30 drops of TEA were added, hydrogen sulfide was introduced into the solution for 10 min. and the reaction mixture was left at room temperature for 2 days. Afterwards, the solvent was evaporated, the residue was dissolved in ethyl acetate and mixed with 1 N HCl. After washing of the organic phase with saturated saline and drying over sodium sulfate, the solvent was evaporated. 2.38 g of the thioamide obtained in this way was dissolved in 100 ml of acetone, 6.5 g of methyl iodide was added to the solution which was then left in the dark for 20 hours at room temperature. Afterwards, the solvent was evaporated, the thioimidoester hydroiodide was dissolved in 50 ml of methanol, 0.5 g of ammonium acetate was added and the mixture was heated for 4 hours at 60° C. in a water bath. The crude product obtained after evaporation of the solvent could be purified over SG 60. Elution was carried out first with chloroform, then with chloroform/methanol 9:1. The amidine hydroiodide purified in this way was converted into hydrochloride over an ion exchanger (Amberlite IRA-420). Yield: 1.45 g of an amorphous powder (56%).

The compounds were characterized by mass spectrometry and tested for purity by TLC and HPLC.

Abbreviations

NMM N-Methylmorpholine

SG 60 Silica gel 60

THF Tetrahydrofuran

HOBt 1-Hydroxy-benzotriazole

DCC Dicyclohexylcarbodiimide

DCU Dicyclohexylurea

LH 20 Sephadex LH 20

TLC Thin layer chromatography

HPLC High pressure liquid chromatography

Inhibition of urokinase by selected compounds

| Configuration | R¹ | R² | n | μmol/l |
|---|---|---|---|---|
| L | —N(piperazine)N—COOC₂H₅ | TIPP | 0 | 0.49 |
| D,L | —N(piperazine)N—COOC₂H₅ | TIPP | 0 | 0.54 |
| D,L | —N(piperidine)—COOC₂H₅ | TIPP | 0 | 0.72 |
| D,L | —N(piperazine)N—COOCH₃ | TIPP | 0 | 0.77 |
| D,L | —N(piperazine)N—COOCH(CH₃)₂ | TIPP | 0 | 0.79 |
| D,L | —N(piperidine)—COOBzl | TIPP | 0 | 1.2 |
| D,L | —N(piperidine)—CONHBzl | TIPP | 0 | 1.5 |
| D,L | —N(piperazine)N—COOBzl | TIPP | 0 | 1.9 |
| D,L | —N(piperidine)—CH₃ | TIPP | 0 | 2.2 |
| D,L | —N(piperidine)—CH₂CONHNH-(2-thienyl) | TIPP | 0 | 2.3 |
| D,L | —N(piperazine)N—CON(CH₃)₂ | TIPP | 0 | 2.7 |
| L | —N(piperidine)—COOC₂H₅ | 2NAPH | 0 | 3.3 |
| D,L | —N(piperazine)N—COCH₃ | TIPP | 0 | 3.5 |
| L | —N(piperidine)—COOBzl | 2NAPH | 0 | 3.9 |
| D,L | —N(piperidine)—CONHCH(CH₃)₂ | TIPP | 0 | 4.2 |
| D,L | —N(piperidine)—CONHCH₃ | TIPP | 0 | 4.4 |

Abbreviations: TIPP=2,4,6-Triisopropylphenyl, 2NAPH=2-Naphthyl, Bzl=Benzyl

Determination of the Inhibitory Activity

To determine the inhibitory activity, 200 μl of Tris buffer (0.05 mol/l, containing the inhibitor, 0.154 mol/l NaCl, 5% ethanol, pH 8.0), 25 μl of substrate (Pefachrome UK or Bz-βAla-Gly-Arg-pNA in H₂O; Pentapharm Ltd., Basel, Switzerland) and 50 μl of sc-urokinase (Ribosepharm GmbH, Haan, Germany) was incubated at 25° C. After 3 min, the reaction was stopped by addition of 25 μl of acetic acid (50%) and the absorption was determined at 405 nm by means of a microplate reader (MR 5000, Dynatech, Denkendorf, Germany). The $K_i$ values were determined according to Dixon by linear regression using a computer program. The $K_i$ values represent the mean from at least 3 determinations, the standard deviation was below 25%.

The invention claimed is:

1. Purified urokinase inhibitors of general formula

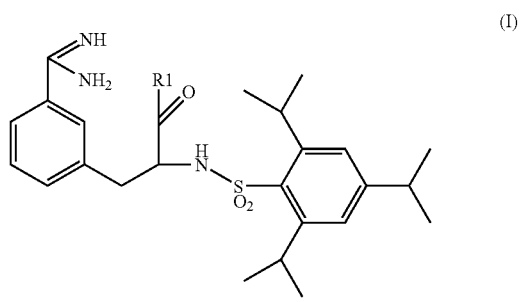

which are present as compounds in L-form, and wherein R¹ represents (a) a group of formula

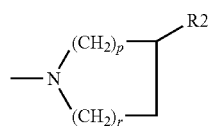

wherein either p=1 and r=2 and R² is benzyloxycarbonyl, benzylaminocarbonyl or 2-thienylhydrazinocarbonyl, or p=2 and r=1 and R² is ethoxycarbonyl, 2-propyloxycarbonyl, 2-propylaminocarbonyl, methylaminocarbonyl or methyl; or (b) a group of formula

wherein R³ is selected from the group consisting of methoxycarbonyl, ethoxycarbonyl, and benzyloxycarbonyl, and wherein the compounds occur in the form of their free bases or as salts with inorganic acids, or as salts with organic acids.

2. A composition comprising the urokinase inhibitor according to claim 1 and a pharmaceutical additive.

3. The composition according to claim 2, wherein said pharmaceutical additive is suitable for administration orally, subcutaneously and/or intravenously.

4. The composition according to claim 2, wherein said composition is in the form of tablets, dragées, capsules, suppositories, solutions or transdermal systems.

5. The purified urokinase inhibitors according to claim 1, wherein said compounds occur in the form of their hydrochlorides.

6. The purified urokinase inhibitors according to claim 1, wherein R¹ is a group of formula:

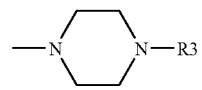

and R³ is ethoxycarbonyl.

* * * * *